United States Patent
Sugo et al.

(10) Patent No.: US 7,402,138 B2
(45) Date of Patent: Jul. 22, 2008

(54) METHOD AND APPARATUS FOR MEASURING BLOOD VOLUME, AND VITAL SIGN MONITOR USING THE SAME

(75) Inventors: Yoshihiro Sugo, Tokyo (JP); Takeshi Akiyama, Tokyo (JP); Keisuke Uchida, Tokyo (JP); Sunao Takeda, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 308 days.

(21) Appl. No.: 11/094,228

(22) Filed: Mar. 31, 2005

(65) Prior Publication Data
US 2005/0222514 A1    Oct. 6, 2005

(30) Foreign Application Priority Data
Mar. 31, 2004   (JP) .......................... P2004-104822

(51) Int. Cl.
*A61B 5/02*   (2006.01)

(52) U.S. Cl. .................................................. 600/526

(58) Field of Classification Search ................ 600/526
See application file for complete search history.

(56) References Cited

U.S. PATENT DOCUMENTS
6,652,466 B2   11/2003 Sugo et al.
2002/0151805 A1 * 10/2002 Sugo et al. ................ 600/504

FOREIGN PATENT DOCUMENTS
JP   2002-253519 A   9/2002

OTHER PUBLICATIONS

G. Rödig, et al., "Continuous cardiac output measurement: pulse contour analysis vs thermodilution technique in cardiac surgical patients", British Journal of Anaesthesia, 1999, pp. 525-530, vol. 82, No. 4.

* cited by examiner

*Primary Examiner*—Carl H. Layno
*Assistant Examiner*—Yun Haeng Lee
(74) *Attorney, Agent, or Firm*—Sughrue Mion, PLLC (57) ABSTRACT

A first member is adapted to measure an electrocardiogram of a patient. A second member is adapted to measure a peripheral pulse wave of the patient. A first calculator calculates a pulse wave propagation time (PWTT) and a heart rate (HR) of the patient based on the electrocardiogram and the peripheral pulse wave. A second calculator calculates a cardiac output (CO) of the patient with an equation of CO=($\alpha$K·PWTT+$\beta$K)· HR, where $\alpha$, $\beta$ and K are coefficients inherent to the patient.

3 Claims, 13 Drawing Sheets

METHOD AND APPARATUS FOR MEASURING BLOOD VOLUME, AND VITAL SIGN MONITOR USING THE SAME

BACKGROUND OF THE INVENTION

The present invention relates to a method and an apparatus for measuring blood volume ejected by cardiac contraction, and a vital sign monitor using such method and apparatus.

In medical facilities, variation in the hemodynamics of a patient in an operating room, an intensive care unit (ICU), an emergency room, a dialysis treatment room or the like needs to be monitored continuously as long as possible.

Conventionally, monitoring of the variation in the hemodynamics of such a patient has been predominantly carried out by direct monitoring of a blood pressure.

In a living body, a cardiac output and a vascular resistance are regulated such that the blood pressure of the centrum is limited within a predetermined range.

Therefore, in order to know the variation in the hemodynamics of a patient at an early stage, it is not enough to only monitor the blood pressure directly, and there is a need to know cause of change in the blood pressure when the change in the blood pressure is observed. For this reason, there is a need to monitor a change in the cardiac output, in addition to monitoring the change in the blood pressure.

As methods of measuring the change in the cardiac output to monitor the variation in the hemodynamics of a patient, there are conventional methods such as a thermodilution method, a dye dilution method, an ultrasound method and the like, which will be described below.

First, the thermodilution method will be discussed. In this method, a Swan-Ganz catheter is inserted through a carotid artery, a predetermined amount of cold saline or cold glucose solution is introduced to a vena cava or a right atrium, and the cardiac output resulting from a temperature change is measured in a pulmonary artery.

Recently, another thermodilution method has been proposed in which blood is warmed through a catheter, and the cardiac output resulting from a temperature change is measured. According to this method, the cardiac output can be measured automatically at a regular time interval.

Next, the dye dilution method will be discussed. In this method, a predetermined amount of dye is introduced to a vein, and then the dye concentration is measured invasively or non-invasively in a part where the dye is uniformly diluted and thus the concentration becomes constant, so that the cardiac output is measured.

Next, the ultrasound method will be discussed. In this method, an inner diameter of an arterial blood vessel such as the descending aorta and the blood flow rate therein are measured transesophageally using ultrasound, and thus the cardiac output is measured.

The above-described conventional methods of measuring the cardiac output by monitoring the variation in the hemodynamics of a patient have the following problems:

The thermodilution method involves a problem in that the measurement is intermittent and continuous measurements are not allowed. Further, insertion of a catheter in the thermodilution method is highly invasive for a patient and involves a risk of infection and the like. Moreover, a skilled medical person is required to insert a catheter and to conduct the measurement. Recently, a method based on continuous measurements has also been developed in the thermodilution method, however, the method still requires insertion of a catheter, and the above-described problems in connection with the insertion of a catheter cannot be solved.

The dye dilution method also has a problem in that continuous measurements are impossible. Further, the method requires a skilled medical person in the measuring process.

The ultrasound method imposes a burden of stress on a patient because a transducer is attached transesophageally. Recently, a non-invasive measurement performed on the body surface has also been made available as a kind of the ultrasound method, but the continuous measurements are still impossible.

Considering the requirement for an aid of a medical person with advanced skill and the procedures being highly invasive for a patient, none of the methods described above can be conducted easily and continuously, and it is difficult to monitor the variation in the hemodynamics of a patient continuously at all times by these methods.

SUMMARY OF THE INVENTION

It is therefore an object of the invention to provide a blood volume measurement method, in which variation in the hemodynamics of a patient can be monitored invasively and continuously at all times, an aid of a skilled medical person in the insertion of a catheter or the like is not needed, suffering of the patient is lessened, and there is no risk of infection because it is non-invasive.

It is also an object of the invention to provide a blood volume measurement apparatus for embodying the above method with an inexpensive configuration.

It is also an object of the invention to provide a vital sign monitor incorporating such an apparatus.

In order to achieve the above objects, according to the invention, there is provided a method of measuring a blood volume, comprising steps of:

obtaining a pulse wave propagation time (PWTT) of a patient;

obtaining a heart rate (HR) of the patient;

obtaining a cardiac output (CO) of the patient with an equation of $CO=(\alpha K \cdot PWTT + \beta K) \cdot HR$, where $\alpha$, $\beta$ and $K$ are coefficients inherent to the patient.

Preferably, at least one of the coefficients is calibrated with a value obtained by a blood pressure measurement.

Preferably, the pulse wave propagation time is defined as a sum of a pre-ejection period of a heart of the patient, a time period during which a pulse wave generated in an aorta of the patient reaches a peripheral blood vessel where a plethysmogram is measured.

Preferably, the method further comprises a step of administrating a vasoconstrictor. Here, it is preferable that the vasoconstrictor is phynylephine.

According to the invention, there is also provided an apparatus for measuring a blood volume, comprising:

a first member, adapted to measure an electrocardiogram of a patient;

a second member, adapted to measure a peripheral pulse wave of the patient;

a first calculator, which calculates a pulse wave propagation time (PWTT) and a heart rate (HR) of the patient based on the electrocardiogram and the peripheral pulse wave; and a second calculator, which calculates a cardiac output (CO) of the patient with an equation of $CO=(\alpha K \cdot PWTT + \beta K) \cdot HR$, where $\alpha$, $\beta$ and $K$ are coefficients inherent to the patient.

Preferably, the measuring apparatus further comprises a third member, adapted to measure a blood pressure of the patient. At least one of the coefficients is calibrated with a value obtained by the third member.

According to the invention, there is also provided a vital sign monitor comprising the above measuring apparatus, and a display showing at least the cardiac output.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

The principle used in the invention for the measurement of the blood volume ejected by cardiac contraction (cardiac output) will be explained below.

Figure 1:
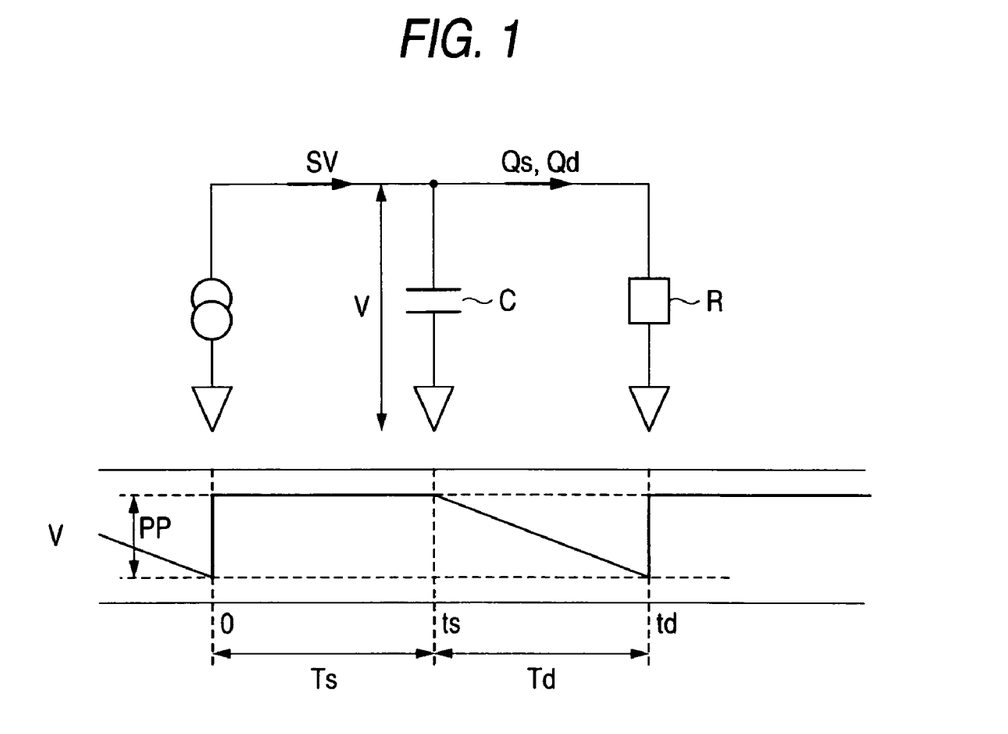
FIG. 1 is a diagram for explaining Windkessel model.

When the Windkessel model as shown in FIG. 1 is used, the influx flow volume to the aorta during a systole, that is, the flow volume (SV−Qs) obtained by deducting the efflux flow volume to the periphery during a systole Qs from the stroke volume SV, is represented by the product of the aortic compliance C with the pulse pressure PP (see Equation 1). In this specification, the term "pulse pressure" means a difference between the systolic blood pressure and the diastolic blood pressure.

$$SV-Qs=C \cdot PP \tag{1}$$

The efflux flow volume to the periphery during a diastole Qd is the same as (SV−Qs). Further, Qs and Qd represent values obtained by dividing the systolic and diastolic arterial pressures V by the vascular resistance R and then multiplying by the systolic duration Ts and the diastolic duration Td, respectively. However, as it is estimated, for the matter of simplicity, that the flow volume values are proportional to Ts and Td, respectively, the values may be represented by Equation 2.

$$Qd=SV-Qs=SV \cdot Td/(Ts+Td) \tag{2}$$

From Equations 1 and 2, Equation 3 is obtained as follows.

$$SV \cdot Td/(Ts+Td)=C \cdot PP$$

$$SV=C \cdot PP \cdot (1+Ts/Td) \tag{3}$$

Here, if $[C \cdot (1+Ts/Td)]$ is represented by K based on the assumption that C and (Ts/Td) remain constant during the measurement period, Equations 4 and 5 are obtained.

$$SV=K \cdot PP \tag{4}$$

$$PP=SV/K \tag{5}$$

As such, according to the Windkessel model, the pulse pressure is directly proportional to SV.

In practice, actually measured pulse pressure PP1 is related to the pulse pressure PP2 (although this is represented by PP in Equation 5, hereinafter it will be represented by PP2), and to the augmentation in the pulse pressure observed upon administration of a vasoconstrictor or the like PP3, as in the following Equation 6.

$$PP1=PP2+PP3 \tag{6}$$

In a case where PP3 is not observed, Equations 4 and 6 lead to:

$$SV=K \cdot PP1 \tag{7}$$

Therefore, SV can be directly measured from the measurement of blood pressure. However, since PP1 already includes PP3 in the administration of a vasoconstrictor or the like, SV would be overestimated. This has been a problem when SV is calculated from the blood pressure.

In "G. Roodig; Continuous cardiac output measurement: pulse contour analysis vs thermodilution technique in cardiac surgical patients British Journal of Anaesthesia 82(4): 525-30 (1999)", with regard to the accuracy in measurement of the apparatus which enables calculation of the stroke output as well as the cardiac output from the waveform of the arterial pressure measured invasively, it is reported that, for a patient admitted to the ICU after a surgery, when the vascular resistance changed by about 60% upon administration of a vasoconstrictor phenylephrine, a remarkably large bias was observed between the measurements by the apparatus described above and the measurements by the cardiac output computer operating in the thermodilution mode used as the standard method, the values of the former being greater than those of the latter. It is also reported that, in that case, there is accordingly a need for re-calibration by the blood volume flowmeter operating in the thermodilution mode. Further, in the administration of a vasoconstrictor, it is known, as an augmentation of the pulse, that the pulse pressure increases by influence of a reflected wave from the periphery, and PP3 corresponds to this augmentation.

In electrocardiography, the pulse wave propagation time (hereinafter, referred to as PWTT), which corresponds to a time taken from the generation of a pulse wave in the heart which is caused by the electric stimulation of the heart to the reach of the propagated pulse wave to the $SpO_2$ measuring site at the periphery, is represented by Equation 8.

$$PWTT=PEP+PWTT1+PWTT2 \tag{8}$$

Figure 6:
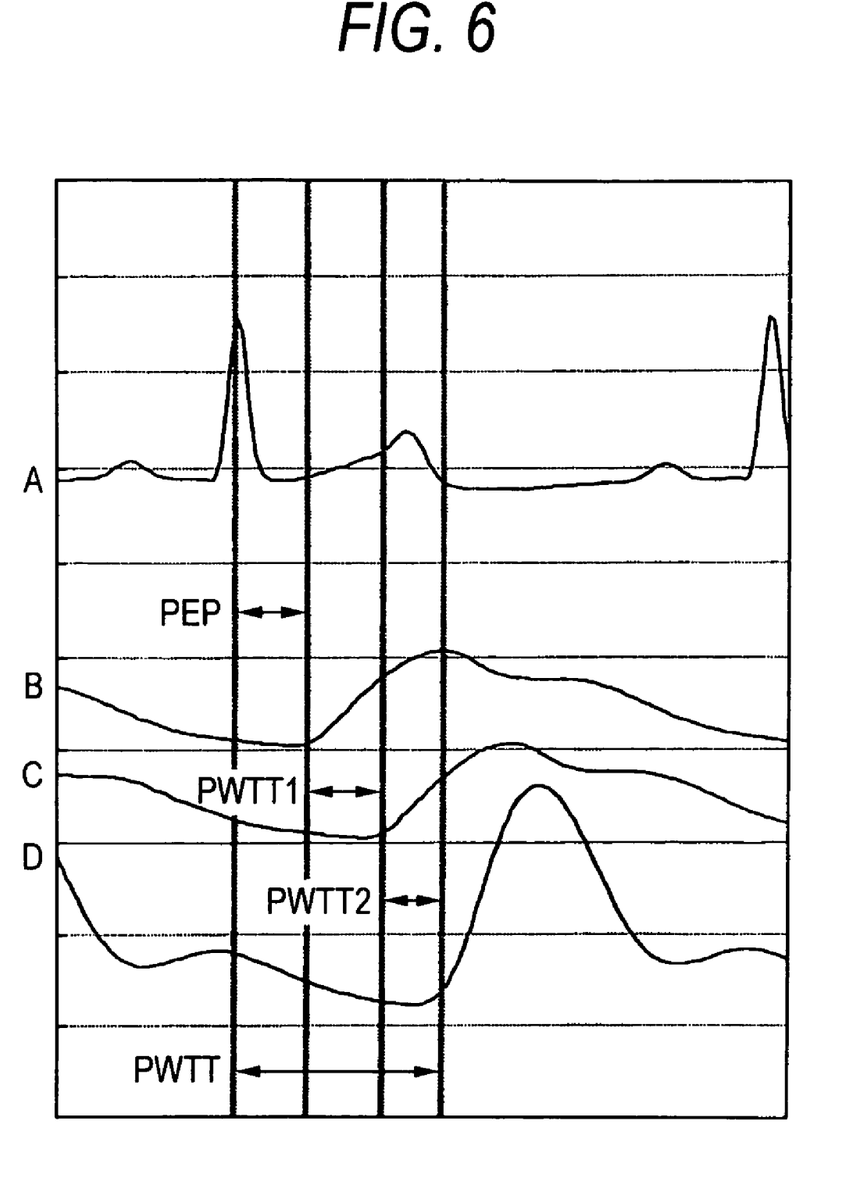
FIG. 6 is a graph showing waveforms of vital signs obtained by a vital sign monitor.

Here, as shown in FIG. 6, PEP is the pre-ejection period of the heart, which is the duration from the initiation of electric stimulation of the heart to the opening of the aortic valve. PWTT1 is a time taken for the pulse wave to be propagated from its generation in the aorta after the opening of the aortic valve to an artery at the periphery where typically blood pressure measurement is conducted invasively. PWTT2 is a time taken for the pulse wave to be further propagated from the artery at the periphery to a peripheral blood vessel where photoplethysmogram is measured.

Figure 2:
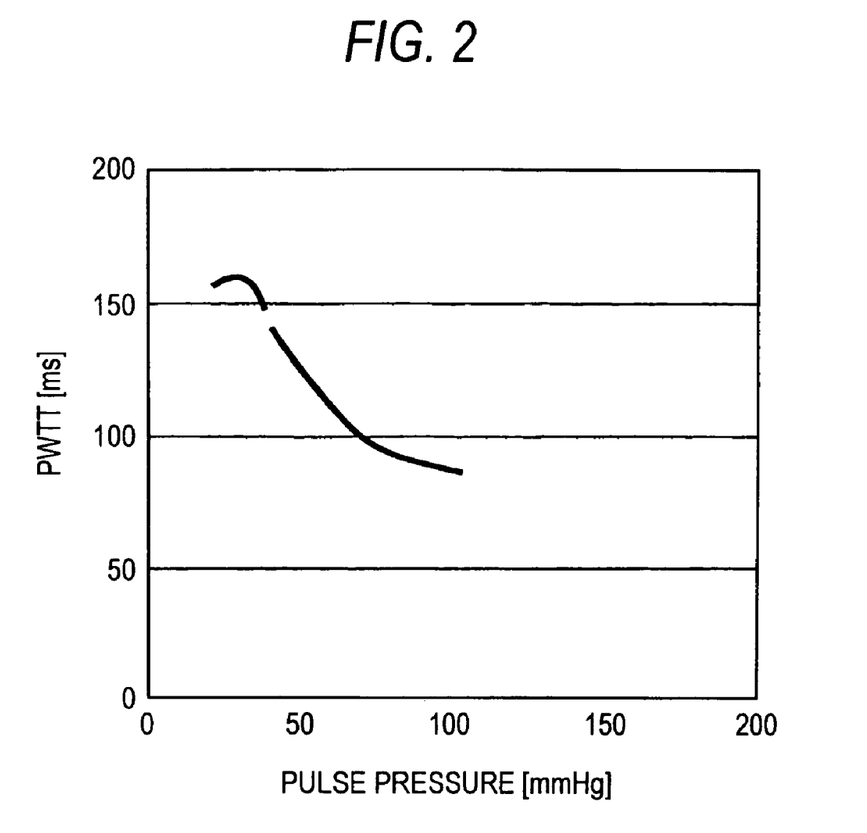
FIG. 2 is a graph showing a typical relationship between a pulse pressure and a pulse wave propagation time.

The duration of (PEP+PWTT1) from the R wave of electrocardiogram (ECG) to the onset of rising in the pulse wave at the femoral artery was measured using ten adult dogs, and measured the relationship between the duration of (PEP+PWTT1) and the pulse pressure with administration of a vasoconstrictor in the respective cases under conditions such as, administration of a vasodilator, increase of the myocardial contractility, attenuation of myocardiac contractility and blood removal. In this way, it is found good correlation between the pulse pressure PP1 and the duration of (PEP+PWTT1). FIG. 2 is a graph showing the representative relationship between the PWTT and the pulse pressure PP.

Therefore, the relationship between the pulse pressure PP1 and (PEP+PWTT1) can be represented by the following Equation 9.

$$PEP+PWTT1=a \cdot PP1+b \tag{9}$$

Further, the relationship between PWTT2 and PP1 is represented by the following Equation 10.

$$PWTT2=C \cdot PP1+d+e \tag{10}$$

Since it has been discovered that, in a case where PP3 appears with the use of a vasoconstrictor, PWTT2 tends to be prolonged as compared to cases under other conditions, a portion corresponding to this prolongation is represented by "e" (where, e is not limited to a constant).

Substituting Equations 9 and 10 for Equation 8, Equation 11 is obtained as follows.

$$PWTT=(a \cdot PP1+b)+(c \cdot PP1+d+e)$$

$$PP1=(PWTT-b-d-e)/(a+c) \tag{11}$$

As PP2 in Equation 6 is replaced with the right-hand side of Equation 5, Equation 12 is obtained.

$$PP1=SV/K+PP3 \tag{12}$$

From Equations 11 and 12, Equation 13 is obtained as follows.

$$[PWTT-(b+d)]/(a+c)=SV/K+PP3+e/(a+c)$$

$$SV=K \cdot \{[PWTT-(b+d)]/(a+c)\}-K \cdot [PP3+e/(a+c)] \tag{13}$$

Figure 5:
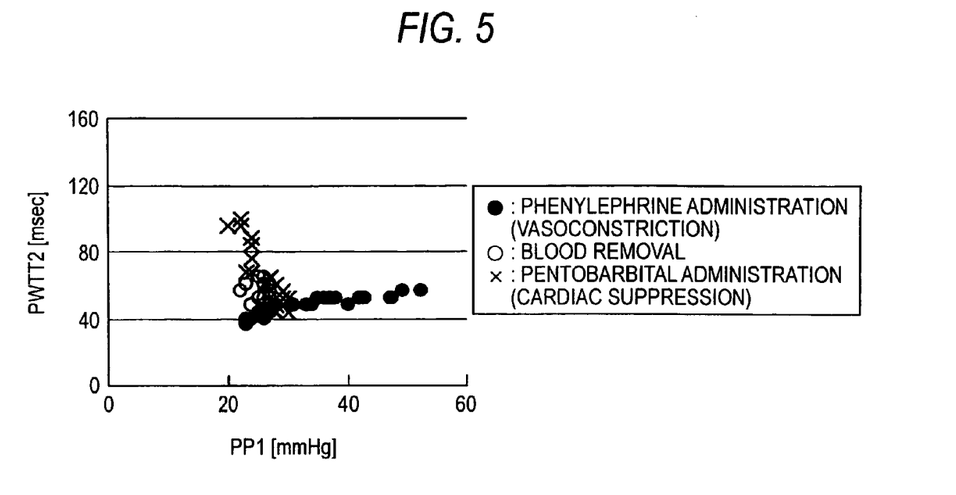
FIG. 5 is a graph showing relationships between the pulse pressure and a time taken for the pulse wave to be propagated from an artery at the periphery to a blood vessel where photoplethysmogram is observed, which are measured in cases of vasoconstriction, blood removal and cardiac suppression.

As described above, it has been experimentally found that PWTT2 tends to be prolonged when PP3 is observed upon use of a vasoconstrictor or the like. FIG. 5 shows this relationship.

When phenylephrine is administered, PP3 is observed and accordingly PP1 is increased, as shown in FIG. 5. However, the relationship between PWTT2 and PP1 which may be observed in cases of blood removal or administration of pentobarbital is no longer observed with the administration of phenylephrine, and PWTT2 shows a tendency to be prolonged.

Figure 4:
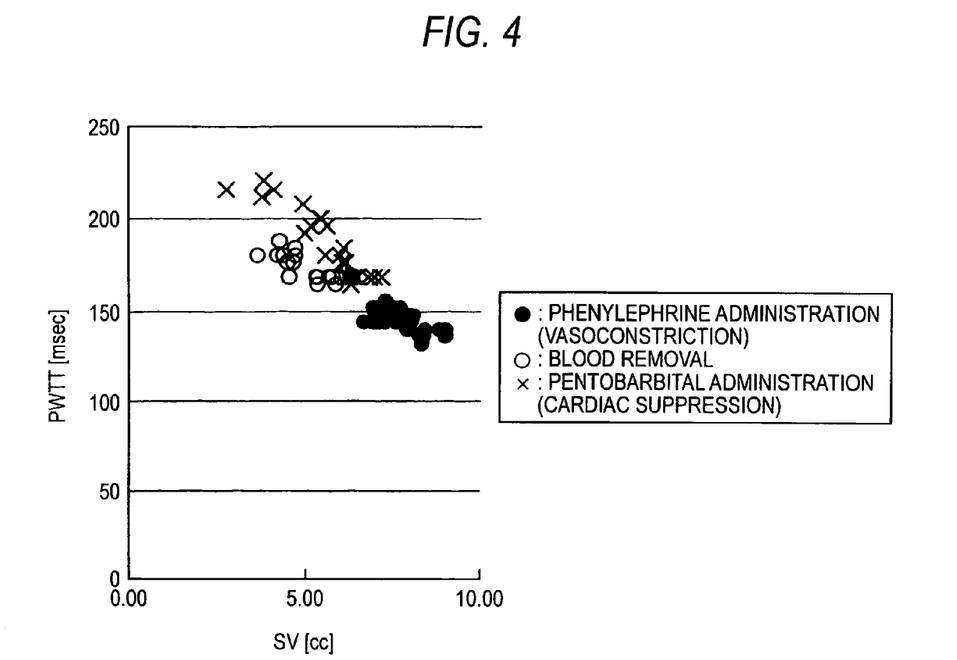
FIG. 4 is a graph showing relationships between a stroke volume and the pulse wave propagation time measured in cases of vasoconstriction, blood removal and cardiac suppression.

Therefore, it has been experimentally discovered that, as shown in FIG. 4, there is maintained a negative correlation between SV and PWTT even upon administration of phenylephrine, which may be still observed under different conditions, and thus the second term in the right-hand side of Equation 13 may be substantially ignored.

Here, taking $1/(a+c)=\alpha$; and $-(b+d)/(a+c)=\beta$, Equation 14 is obtained.

$$SV=K \cdot (\alpha \cdot PWTT+\beta) \tag{14}$$

wherein $\alpha$ and $\beta$ are empirically obtained coefficients that are inherent to a patient.

Moreover, the cardiac output can be calculated from Equation 15.

$$esCO=K \cdot (\alpha \cdot PWTT+\beta) \cdot HR \tag{15}$$

wherein esCO [liters/min] is the cardiac output, K is an empirically obtained constant which is inherent to a patient, and HR is a heart rate of the patient.

In addition, Equation 15 may be substituted in the same way as in Equation 16.

$$esCO=(\alpha K \cdot PWTT+\beta K) \cdot HR \tag{16}$$

wherein $\alpha K$ and $\beta K$ are empirically obtained coefficients which are inherent to a patient.

Figure 3:
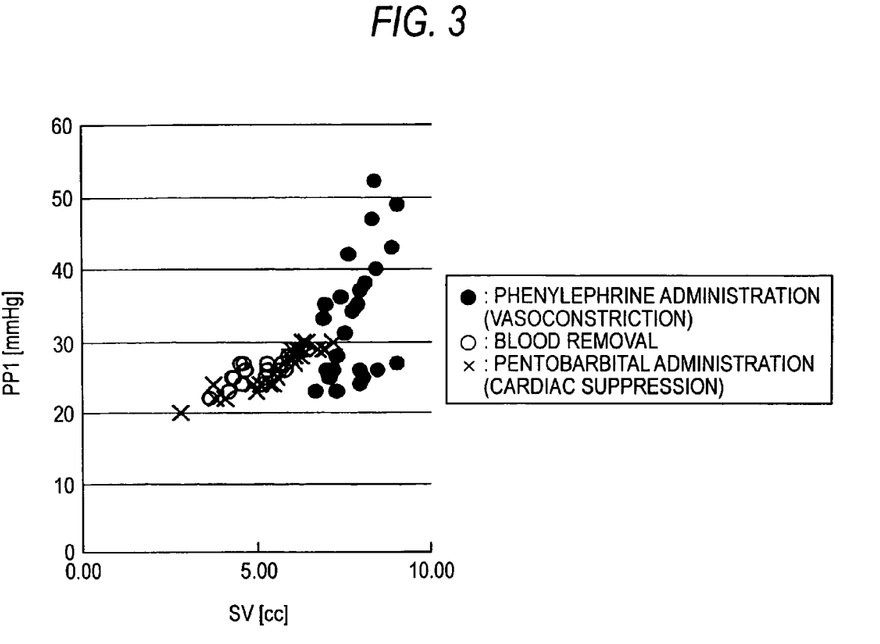
FIG. 3 is a graph showing relationships between a stroke volume and a pulse pressure measured in cases of vasoconstriction, blood removal and cardiac suppression.

When SV and esCO are calculated using PWTT as expressed in Equations 14, 15 and 16, as shown in FIG. 4, there is maintained correlation between SV and PWTT which may be observed under different conditions, even in a case of an augmentation in the pulse pressure associated with the use of a vasoconstrictor, as shown in FIG. 3, and thus problems that can be seen with the conventional practice of calculating SV by blood pressure may be solved. Also, there is no risk of overestimation of CO.

FIGS. 3 and 4 show relationships between SV and PP1 and between SV and PWTT as measured during vascular constriction, blood removal and cardiac suppression in an animal test. Incidentally, there occurred an increase in the vascular resistance by more than 60% upon administration of phenylephrine.

Next, a vital sign monitor according to a first embodiment of the invention will be described below in detail with reference to FIGS. 6 to 9.

Figure 7:
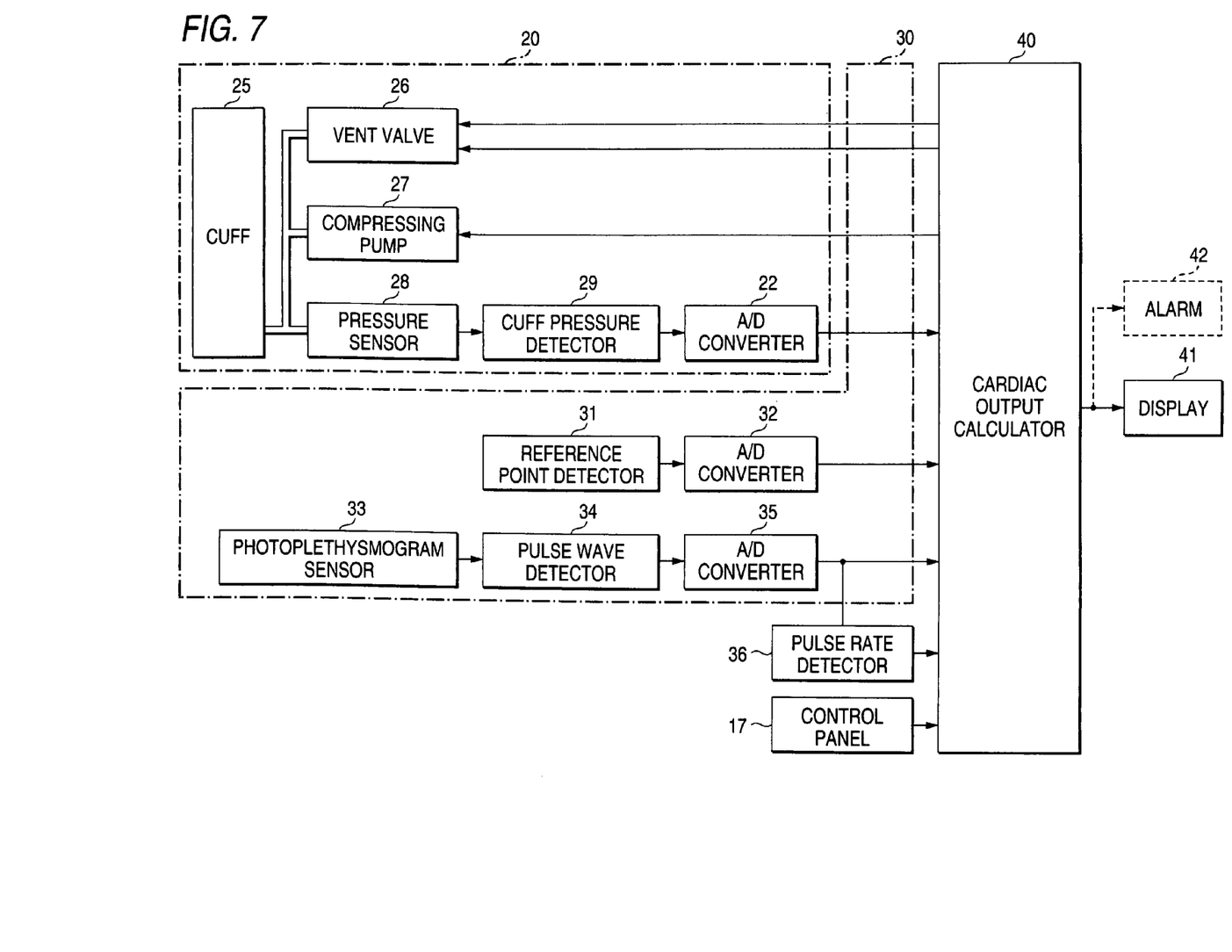
FIG. 7 is a block diagram showing a vital sign monitor according to a first embodiment of the invention.

A blood pressure measuring member 20 comprises a cuff 25, a compressing pump 27, a pressure sensor 28, a cuff pressure detector 29, an A/D converter 22, as shown in FIG. 7.

Figure 8:
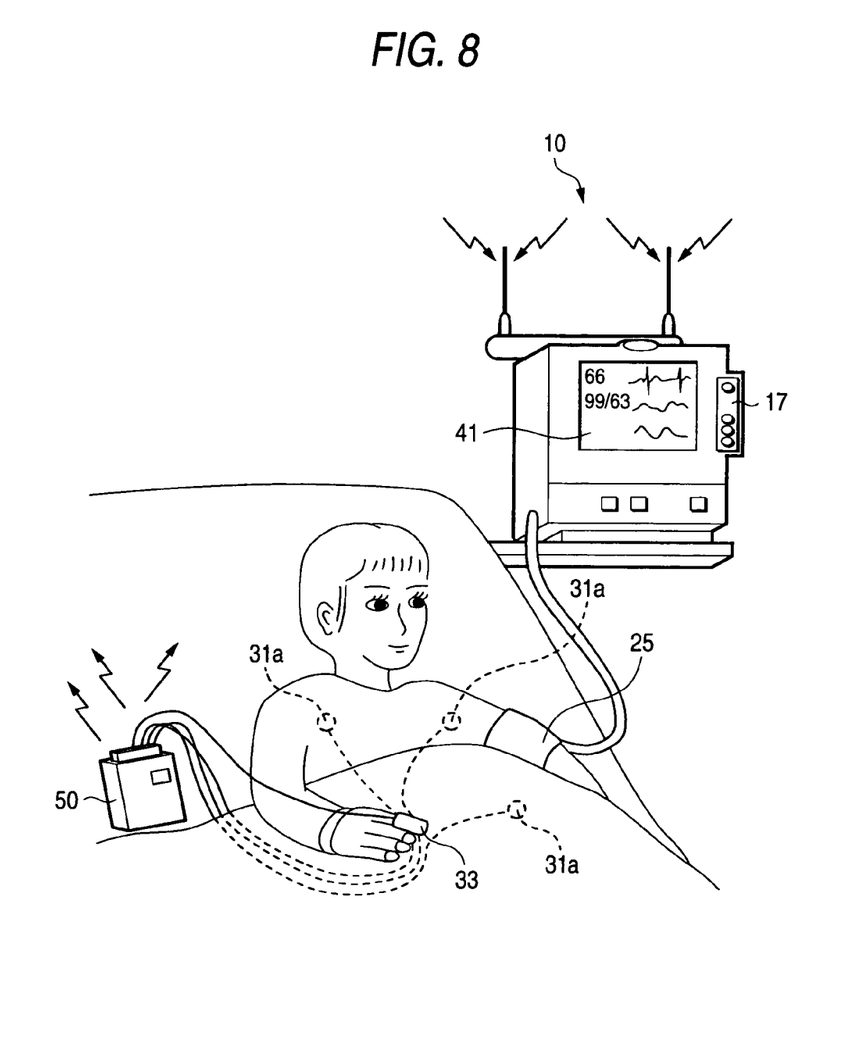
FIG. 8 is a view showing a case where the vital sign monitor of FIG. 7 is applied to a patient.

Specifically, the cuff 25 is attached to an upper arm of a patient for measurement, as shown in FIG. 8. In the cuff 25, the interior is opened or closed with respect to the atmosphere by an exhaust valve 26 installed in a main body of the vital sign monitor 10. Air is supplied to the cuff 25 by the compressing pump 27 installed in the main body of the vital sign monitor 10. The pressure sensor 28 is mounted in the main body of the vital sign monitor 10, and an output of the sensor is detected by the cuff pressure detector 29. An output of the cuff pressure detector 29 is converted into a digital signal by A/D converter 22 and is input to a cardiac output calculator 40. In this embodiment, the cuff pressure detector 29, the A/D converter 22 and the cardiac output calculator 40 are installed in the main body of the vital sign monitor 10.

In FIG. 6, "A" designates an electrocardiogram (ECG) waveform, and "B" designates a waveform of an aortic pressure wave immediately after the ejection from the heart. "C" and "D" designate a waveform of an arterial pressure wave at the periphery and a waveform of photoplethysmogram of a peripheral artery, respectively.

A PWTT measuring member 30 comprises a reference point detector 31, an A/D converter 32, a photoplethysmogram sensor 33, a pulse wave detector 34, and an A/D converter 35. An output signal of the AND converter 35 is input to a pulse rate detector 36.

The reference point detector 31 is provided to detect a point of time when an R wave is generated on an ECG, and an output thereof is converted into a digital signal by the A/D converter 32 and then is input to the cardiac output calculator 40. Specifically, the reference point detector 31 comprises ECG electrodes 31a which are attached to the chest of a patient, as illustrated in FIG. 8.

Measurement data is transmitted from a transmitter 50 which is electrically connected to those ECG electrodes 31a to the main body of the vital sign monitor 10 in a wireless manner. The transmitted measurement data is converted into a digital signal by the A/D converter 32 in the main body of the vital sign monitor 10 and then are input to the cardiac output calculator 40. In this way, the ECG waveform A as shown in FIG. 6 is obtained.

Meanwhile, the photoplethysmogram sensor 33 is intended to be attached to a peripheral part, such as a finger, of a patient, as shown in FIG. 8, and to be used in obtaining the PWTT, for example, by performing $SpO_2$ measurement. The photoplethysmogram sensor 33 is electrically connected to the transmitter 50 so that the measurement data is transmitted to the main body of the vital sign monitor 10 in a wireless manner.

When the measurement data is sent to the pulse wave detector 34 in the main body of the vital sign monitor 10, the pulse wave (photoplethysmogram) at a location where the photoplethysmogram sensor 33 is attached to the patient is detected. The output of the pulse wave detector 34 is converted into a digital signal by the A/D converter 35 and then is input to the cardiac output calculator 40. As such, a waveform of the photoplethysmogram (a waveform at the periphery) D shown in FIG. 6 are obtained.

Figure 9:
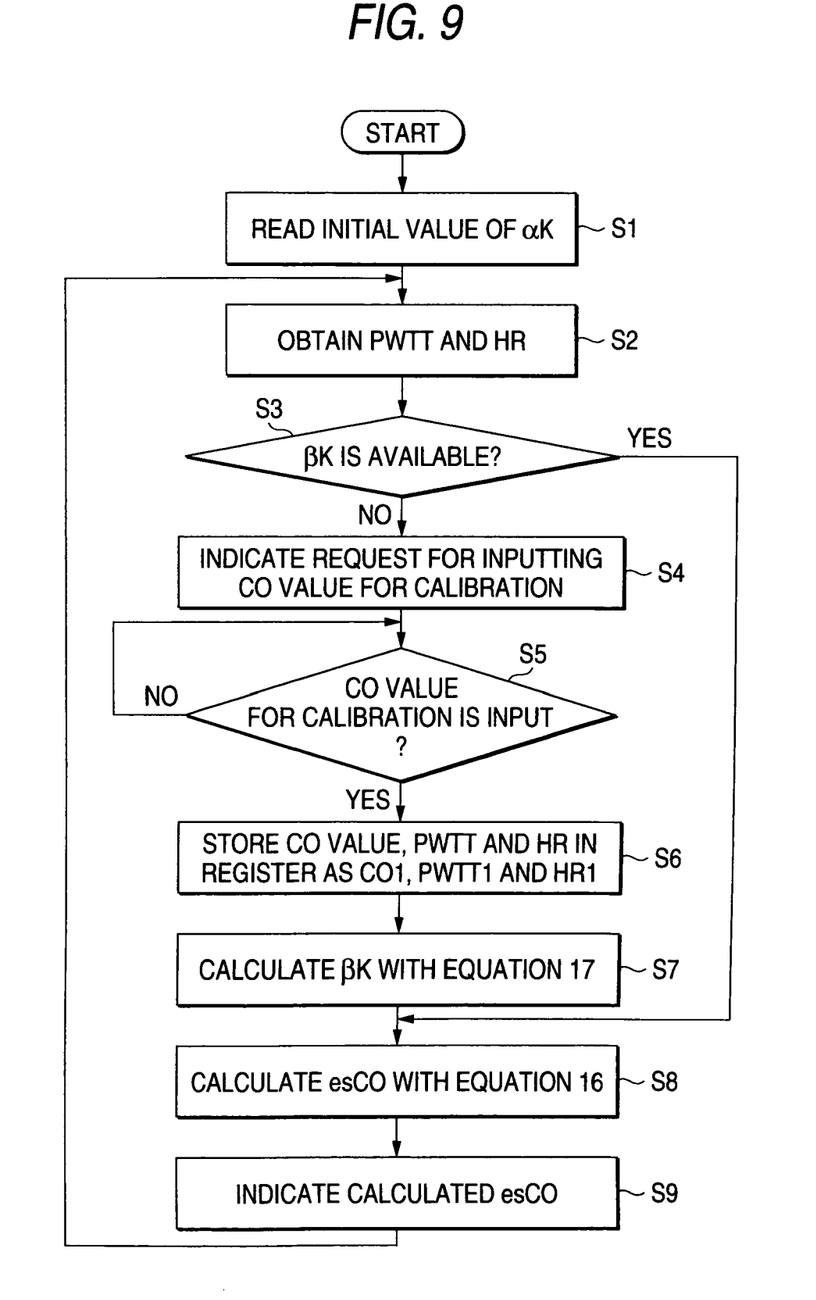
FIG. 9 is a flow chart showing a procedure for obtaining a cardiac output, which is executed in the vital sign monitor of FIG. 7.

Next, procedures to obtain esCO from the above Equation 16 will be explained with reference to FIG. 9.

In this embodiment, $\beta K$ is obtained by calibration using an initial value of $\alpha K$ and then the esCO is calculated.

Reading of the initial value of $\alpha K$ is carried out (Step S1). PWTT and HR are obtained (Step S2). It is determined whether $\beta K$ is available (Step S3). If the determination in Step S3 is NO, then a request for input of cardiac output (CO) value for calibration is indicated on a display 41 of the vital sign monitor 10 (Step S4). It is determined whether the CO value for calibration has been input through a control panel 17 of the vital sign monitor 10 (Step S5). If the determination in Step S5 is YES, the input CO value, the obtained PWTT and HR values are stored in a register as CO1, PWTT1 and HR1, respectively (Step S6). $\beta K$ is obtained by Equation 17 (Step S7).

$$\beta K = CO1/HR1 - \alpha K \cdot PWTT1 \quad (17)$$

Using thus obtained $\beta K$, esCO is calculated with Equation 16 (Step S8). If the determination in Step S3 is YES, likewise, esCO is calculated with Equation 16 (Step S8). The esCO obtained from the computation is indicated on a display 41 (Step S9). The above procedure is repeated as required.

Figure 10:
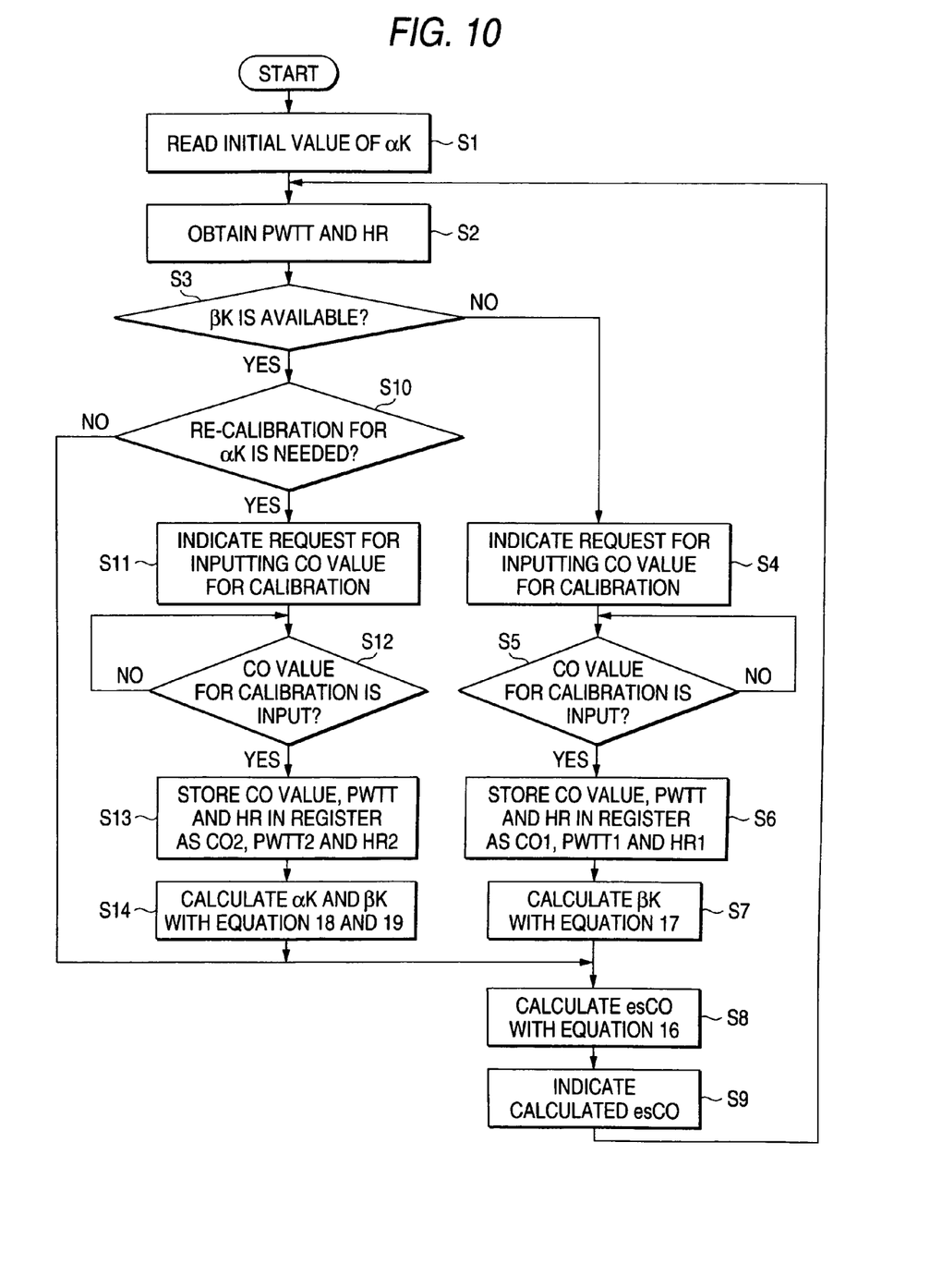
FIG. 10 is a flow chart showing a procedure for obtaining a cardiac output, according to a second embodiment of the invention.

FIG. 10 shows a procedure for obtaining esCO according to a second embodiment of the invention. In this embodiment, $\alpha K$ and $\beta K$ are obtained by calibration and the esCO is then calculated. Same operations as those in the first embodiment will be designated by the same reference numerals, and repetitive explanations for those will be omitted.

In this embodiment, if the determination in Step S3 is YES, it is determined whether re-calibration for $\alpha K$ should be carried out (Step S10). If the determination in Step S10 is NO, the esCO is calculated with Equation 16 (Step S8). If the determination in Step S10 is YES, a request for input of the CO value for calibration is indicated on the display 41 (Step S11). It is determined whether the CO value for calibration has been input through the control panel 17 (Step S12). If the determination in Step S12 is YES, the input CO value, the obtained PWTT and HR values are stored in the register as CO2, PWTT2 and HR2, respectively (Step S13). $\alpha K$ and $\beta K$ are calculated with Equations 18 and 19 (Step S14).

$$CO1 = (\alpha K \cdot PWTT1 + \beta K) \cdot HR1 \quad (18)$$

$$CO2 = (\alpha K \cdot PWTT2 + \beta K) \cdot HR2 \quad (19)$$

Using thus obtained $\alpha K$ and $\beta K$, esCO is calculated with Equation 16 (Step S8). If the determination in step S10 is NO, similarly, esCO is calculated with Equation 16 (Step S8). The esCO obtained from the computation is indicated on the display 41 (Step S9). The above procedure is repeated as required.

Figure 11:
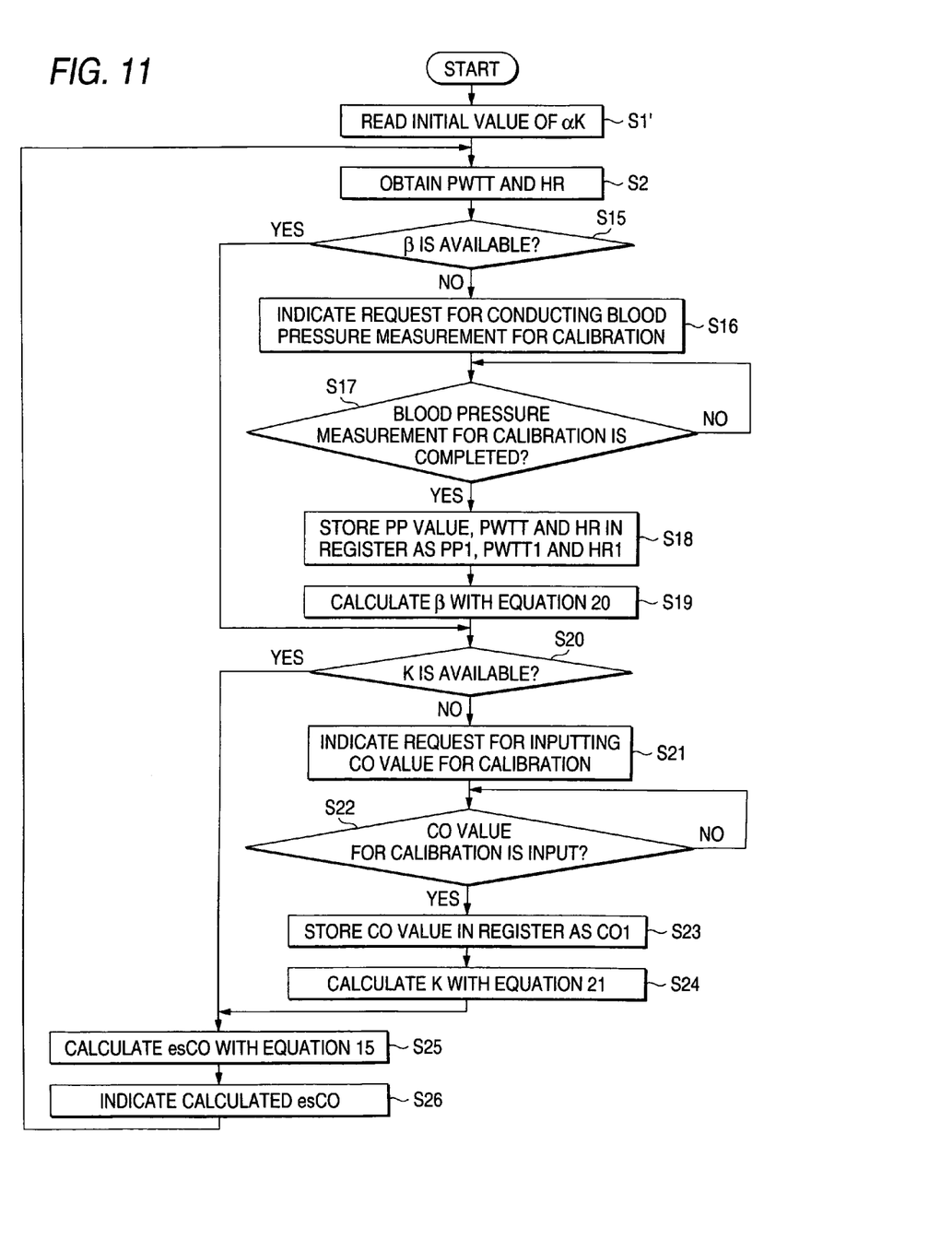
FIG. 11 is a flow chart showing a procedure for obtaining a cardiac output, according to a third embodiment of the invention.

FIG. 11 shows a procedure for obtaining esCO according to a third embodiment of the invention. In this embodiment, $\beta$ and K are obtained by calibration using an initial value of $\alpha$ and then the esCO is calculated. Calibration for $\beta$ is carried out only when there is no augmentation of pulse pressure resulting from an administration of vasoconstrictor or the like. Same operations as those in the first embodiment will be designated by the same reference numerals, and repetitive explanations for those will be omitted.

First, reading of the initial value of $\alpha$ is carried out (Step S1'). It is then determined whether $\beta$ is available (Step S15). If the determination in Step S15 is NO, then a request for measurement of blood pressure for calibration is indicated on the display 41 (Step S16). It is determined whether measurement of the blood pressure for calibration has been conducted (Step S17). If the determination in Step S17 is YES, the measured pulse pressure (PP) value, the obtained PWTT and HR values are stored in the register as PP1, PWTT1 and HR1, respectively (Step S18). $\beta$ is calculated with Equation 20 (Step S19).

$$\beta = PP1 - \alpha \cdot PWTT1 \quad (20)$$

If the determination in Step S15 is YES and after $\beta$ is calculated in Step S19, it is determined whether K is available (Step S20). If the determination in Step S20 is NO, a request for input of CO value for calibration is indicated on the display 41 (Step S21). It is determined whether the CO value for calibration has been input through the control panel 17 (Step S22). If the determination in Step S22 is YES, the input CO value is stored in the register as CO1 (Step S23). K is calculated with Equation 21 (Step S24).

$$K = CO1/(\alpha \cdot PWTT1 + \beta) \cdot HR1 \quad (21)$$

If the determination in Step S20 is YES and after K is calculated in Step S24, esCO is calculated with Equation 15 (Step S25), and indicated on the display 41 (Step S26). The above procedure is repeated as required.

Figure 12:
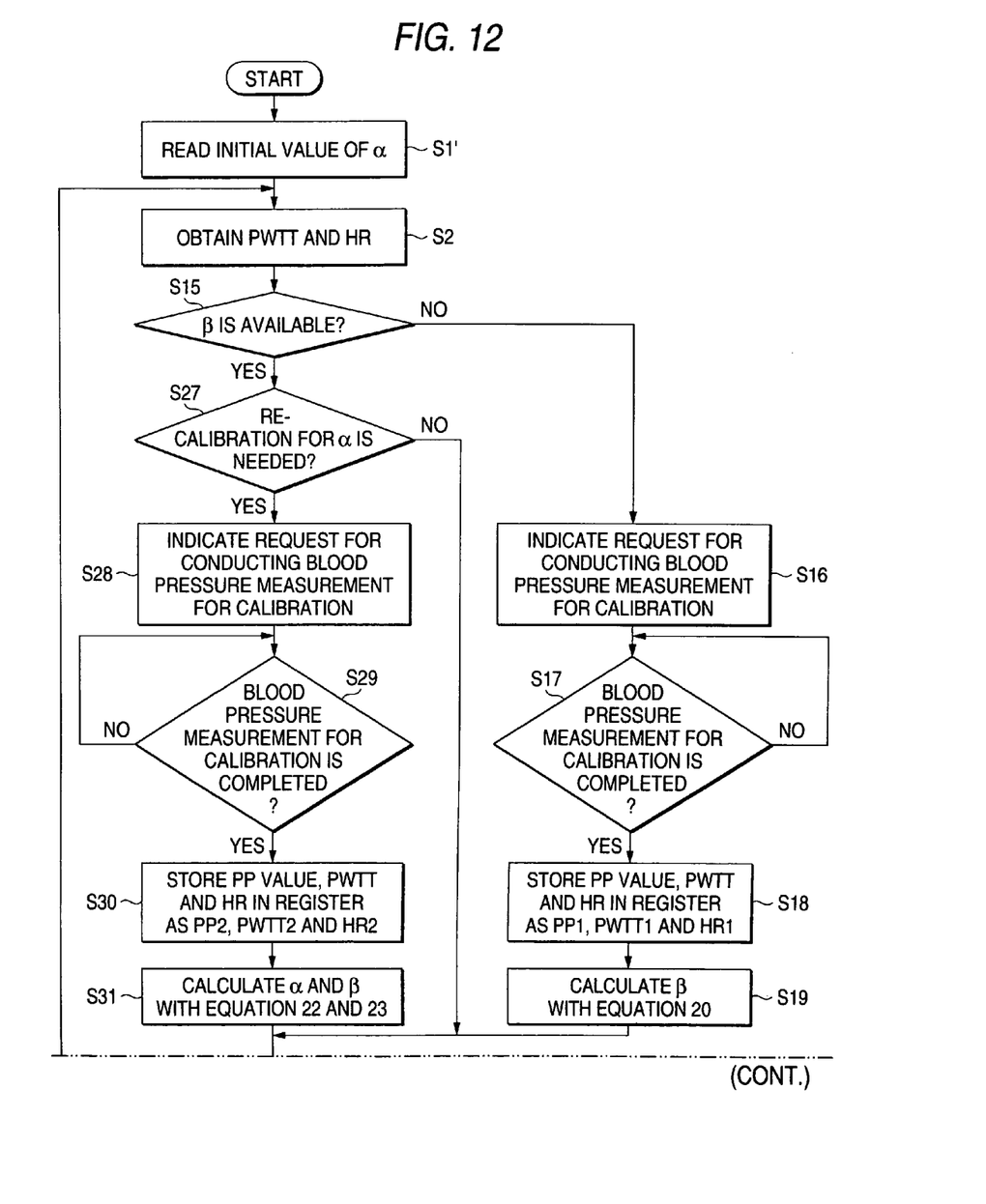
FIG. 12 is a flow chart showing a procedure for obtaining a cardiac output, according to a fourth embodiment of the invention.

FIG. 12 shows a procedure for obtaining esCO according to a fourth embodiment of the invention. In this embodiment, $\alpha$, $\beta$ and K are obtained by calibration and then the esCO is calculated. Calibration for $\alpha$ and $\beta$ is carried out only when there is no augmentation of pulse pressure resulting from an administration of vasoconstrictor or the like. Same operations as those in the third embodiment will be designated by the same reference numerals, and repetitive explanations for those will be omitted.

In this embodiment, if the determination in Step S15 is YES, it is determined whether re-calibration for a is needed (Step S27). If the determination in Step S27 is YES, a request for measurement of blood pressure for calibration is indicated (Step S28). It is determined whether measurement of the blood pressure for calibration has been conducted (Step S29). If the determination in Step S29 is YES, the measured PP value, the obtained PWTT and HR values are stored in the register as PP2, PWTT2 and HR2, respectively (Step S30). $\alpha$ and $\beta$ are calculated with Equations 22 and 23 (Step S31).

$$PP1 = \alpha \cdot PWTT1 + \beta \quad (22)$$

$$PP2 = \alpha \cdot PWTT2 + \beta \quad (23)$$

If the determination in Step S27 is NO and after Step S19 and Step S31 are carried out, it is determined whether K is available (Step S20). The above procedure is repeated as required.

Here, it is also possible to input a blood pressure value measured by another sphygmomanometer through the control panel 17, without conducting the blood pressure measurement for calibration.

In the above embodiments, peripheral pulse wave is represented by photoplethysmogram. However, it may be represented by plethysmogram.

In the above embodiments, the request message are indicated on the display 41 of the vital sign monitor 10. However, such a message is provided by way of an alarm 42 (see FIG. 7).

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. An apparatus for measuring a blood volume, comprising:
    a first member, adapted to measure an electrocardiogram of a patient;
    a second member, adapted to measure a peripheral pulse wave of the patient;
    a first calculator, which calculates a pulse wave propagation time (PWTT) and a heart rate (HR) of the patient based on the electrocardiogram and the peripheral pulse wave; and
    a second calculator, which calculates a cardiac output (CO) of the patient with an equation of CO=($\alpha$K·PWTT+$\beta$K)·HR, where $\alpha$, $\beta$ and K are coefficients inherent to the patient.

2. The measuring apparatus as set forth in claim 1, further comprising a third member, adapted to measure a blood pressure of the patient,
    wherein at least one of the coefficients is calibrated with a value obtained by the third member.

3. A vital sign monitor incorporating the measuring apparatus as set forth in claim 1, the vital sign monitor comprising a display showing at least the cardiac output.

\* \* \* \* \*